United States Patent
Volk

Patent Number: 5,173,723
Date of Patent: Dec. 22, 1992

[54] ASPHERIC OPHTHALMIC ACCOMMODATING LENS DESIGN FOR INTRAOCULAR LENS AND CONTACT LENS

[76] Inventor: Donald A. Volk, 9378 Jackson Ave., Mentor, Ohio 44060

[21] Appl. No.: 591,706

[22] Filed: Oct. 2, 1990

[51] Int. Cl.⁵ .................. G02C 7/04; G02B 13/18; A61F 2/16
[52] U.S. Cl. .................. 351/161; 359/718; 359/720; 623/6
[58] Field of Search .............. 351/160 R, 160 H, 161, 351/162; 623/6; 359/708, 718, 720

[56] References Cited

U.S. PATENT DOCUMENTS

| | | | |
|---|---|---|---|
| 3,751,138 | 8/1973 | Humphrey | 350/432 |
| 4,798,609 | 1/1989 | Grendahl | 351/161 X |
| 4,923,296 | 5/1990 | Erickson | 351/161 |

*Primary Examiner*—Scott J. Sugarman
*Attorney, Agent, or Firm*—Oldham, Oldham, Wilson Co.

[57] ABSTRACT

A multifocal lens configuration is disclosed having a lens body with first and second surfaces wherein at least one of the surfaces is defined three dimensionally as being rotationally non-symmetric about the optical axis of the lens. The lens surface may be described and modeled as having angular zones or sectors of differing curvature responsible for near, intermediate or distance vision or combinations thereof. The lens surface is defined by a plurality of individually defined semi-meridian sections radiating centrifugally from the apical umbilical point or polar axis of the lens surface, wherein each of the semi-meridian sections are tangent to one another at the apical umbilical point and form a continuous smooth surface in conjunction with one another. Each of the semi-meridian sections may be differently and uniquely shaped, and are defined according to shape and magnitude, wherein the semi-meridian sections within an angular zone may be constant or may vary in a continuous and regular manner. The lens configuration will provide an accommodative affect simulating that of the non-presbyopic phakic eye over a full range of distance regardless of the size of the pupillary aperture. The lens configuration can be used in the design on an intraocular lens wherein one or both surfaces of the lens body is provided with the novel surface, or alternatively in contact lens design in a similar manner.

22 Claims, 5 Drawing Sheets

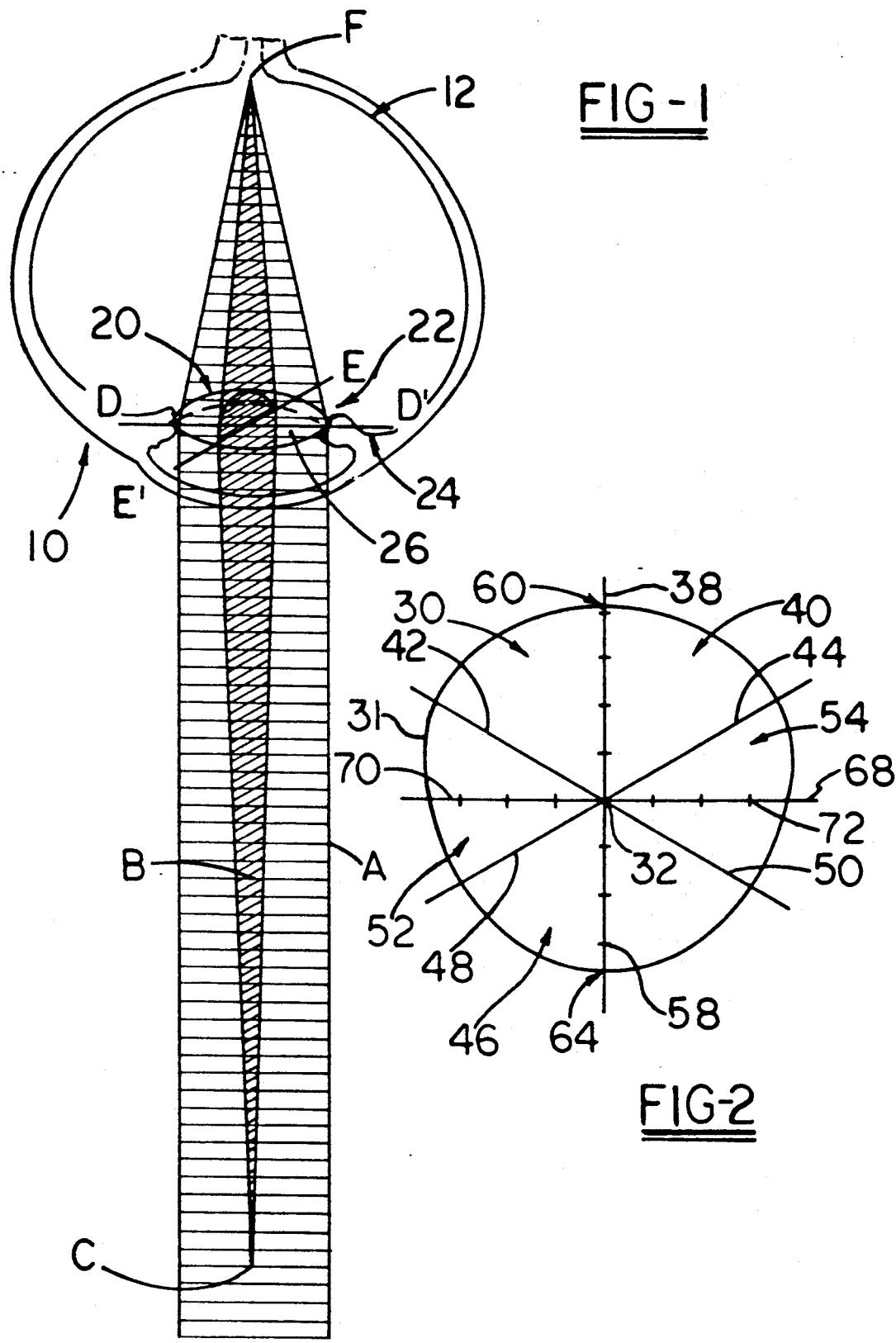

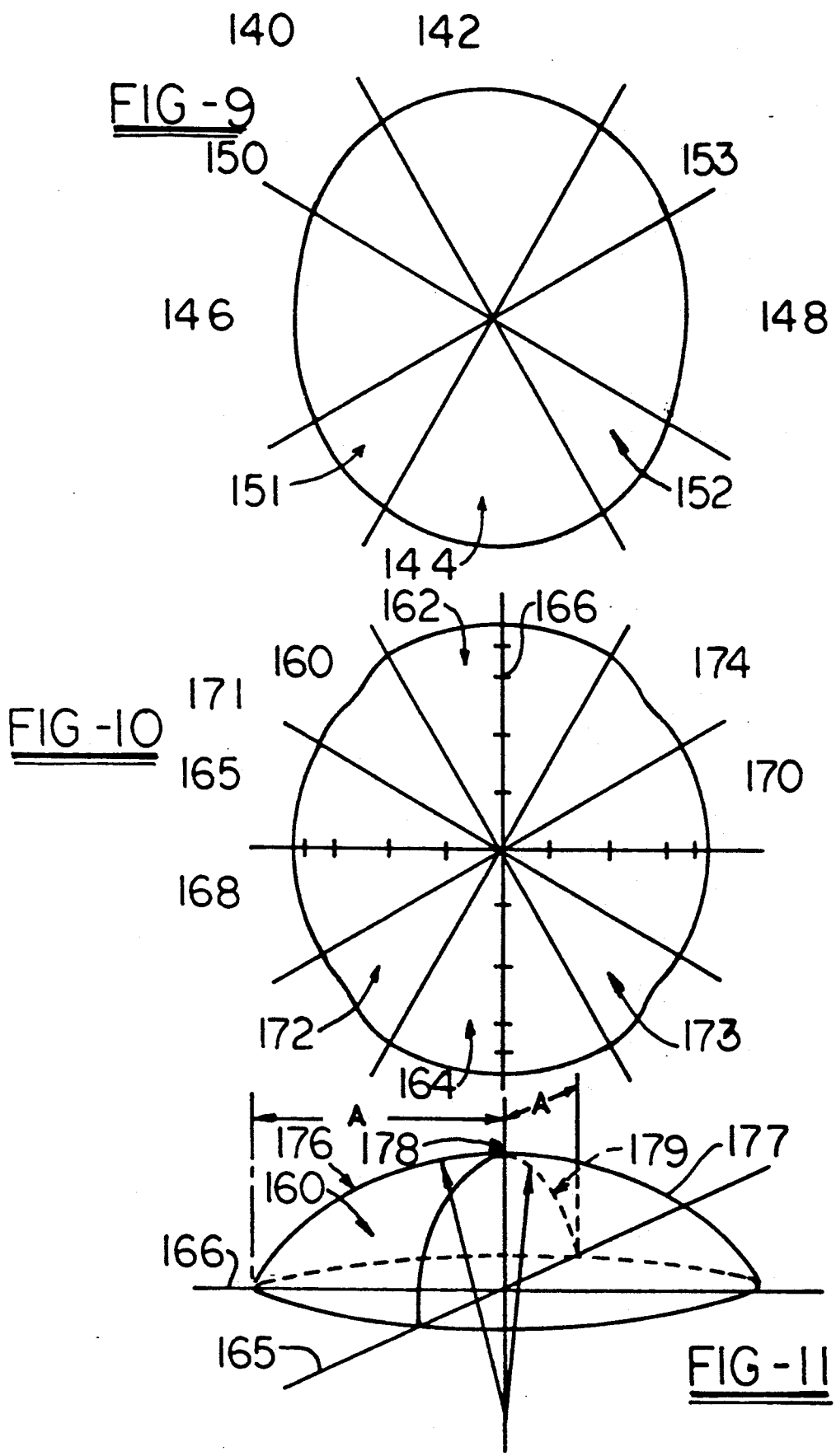

ASPHERIC OPHTHALMIC ACCOMMODATING LENS DESIGN FOR INTRAOCULAR LENS AND CONTACT LENS

TECHNICAL FIELD

The present invention relates to an aspheric ophthalmic lens configuration and specifically to an improved aspheric intraocular or contact lens designed to provide correction of the refractive error of the eye while simultaneously providing an accommodative effect simulating that of the phakic non-presbyopic eye, resulting in clear central vision for the aphakic or presbyopic patient over a full range of distances, regardless of the size of the pupillary aperture. The ophthalmic lens design is characterized as having at least one surface rotationally non-symmetrical about the optical axis of the lens, with defined angular zones of distinct or varying curvature responsible for near, intermediate, or distance vision or combinations thereof.

BACKGROUND OF THE INVENTION

Substantially parallel light rays proceeding from an object viewed at a distance and entering the emmetropic or optically normal eye are brought to focus on the retina. When the object viewed is six meters or more from the eye, the ciliary muscle is relaxed and light rays entering the eye from distant objects are focused on the retina. When such relaxation is maintained, diverging light rays from objects closer to the observer would establish their focus behind the retina. Light rays proceeding from objects closer than six meters are brought to focus on the retina as a result of an increase in the curvature or refractive power of the crystalline lens in the human eye. This physiologic process by which the form and density of the crystalline lens is changed is called accommodation, and ideally results in clear central vision over a full range of distances. The failing or absence of accommodation resulting in presbyopia and the lack of accommodation in an aphakic eye may be addressed in the design of the contact lens or intraocular lens which corrects the refractive error and in some manner and to some degree the accommodative insufficiency or absence of accommodation in the presbyopic or aphakic patient. Numerous contact lens and intraocular lens designs have been proposed to provide an accommodative effect similar in various respects to that of physiologic accommodation.

In U.S. Pat. No. 4,580,882, a continuously variable contact lens is described incorporating a concave aspheric surface of revolution and which has continuously varying refractive power extending from the center region of the lens peripheralward. In this lens design, the refractive power to achieve the desired distance vision correction is located in the center region of the lens with the power increasing peripheralward, up to 9.7 mm in diameter, to the desired near vision power. A problem exists in that such a lens design assumes a maximum pupillary aperture to achieve the desired refractive power for both distance and near vision requirements. It should be evident that such an assumption is not valid under many circumstances and the benefits of such a lens design will degrade accordingly, dependent upon actual conditions encountered by the patient.

In U.S. Pat. No. 4,418,991, a presbyopic contact lens is described as having a spherical anterior surface and a posterior surface of revolution with an annular fitting region as well as an optical region having a central portion providing the distance correction, with a paracentral portion providing a gradient of diopter adds for close and intermediate viewing. In the paracentral portion, the increasing radii of curvature away from the center results in a gradient of diopter add achieved by a continuous flattening of the paracentral area away from the center to between 4 mm and 5½ mm. As stated in this patent, the pupil of the eye has a diameter of about 4 mm to 5 mm in an indoor situation, but may be significantly smaller in conditions where there is a greater amount of light. In normal daylight conditions, the iris aperture may be reduced to from about 2 mm to 3 mm. Again, it should be evident that although the optical area of the lens in this prior invention is designed in an attempt to provide multifocal capabilities, limitations exist with respect to the pupillary aperture which will physically vary depending upon the conditions the wearer encounters, thereby effecting the focusing qualities of the lens.

Similarly, intraocular lenses are implanted in the eye as a replacement of the absent human crystalline lens. In U.S. Pat. No. 4,710,193, an aspheric posterior chamber intraocular lens is described which has at least one convex aspheric surface of revolution designed to provide continuously and regularly increasing refractive power from its apex peripheralward in its optically active area. This invention is stated to correct the axial refractive error of the aphakic eye and to produce clear central vision over a continuous range of distances from near to far. Similar problems exist with regard to the desired refractive correction characteristics of this intraocular lens design with respect to changes in the size of pupillary aperture.

SUMMARY OF THE INVENTION

Based upon the foregoing, there is found to be a need to provide a multifocal lens configuration which provides an accommodative effect simulating that of the non-presbyopic phakic eye, thereby resulting in clear central vision over a continuous range of distances ranging from far to near. This optical effect should be achieved over the described full range of distances, regardless of the size of the pupillary aperture. It is therefore a main object of the present invention to provide a multifocal lens configuration which will provide the aphakic or presbyopic patient clear central vision over a continuous range of distances from far to near, regardless of the size of the pupillary aperture.

Another object of the invention is to provide a multifocal lens configuration wherein one or both surfaces of the lens is defined by semi-meridian sections which are aspheric or transitional in curvature acting to significantly reduce astigmatism, chromatic and especially spherical aberrations.

It is another object of the invention to provide a multifocal lens configuration for use as a contact lens, wherein one or both surfaces of the lens incorporates the novel surface design of the invention.

It is another object of the invention to provide a multifocal lens configuration for use in an intraocular lens, wherein one or both surfaces of the lens incorporates the novel surface design of the invention.

Another object of the invention is to provide the multifocal lens configuration having one or both surfaces thereon including variable power which is defined in angular rather than annular zones to give clear vision over a range of distances from six meters and beyond to as close as thirty centimeters as desired.

Yet another object of the invention is to provide a multifocal lens configuration wherein one or both surfaces of the lens incorporating the invention have defined angular zones wherein each of the defined angular zones has variable power which contribute to the correction of the refractive error of the eye for a particular distance range.

Yet another object the invention is to provide a multifocal lens configuration wherein one or both surfaces of the lens incorporating the invention have defined angular distance and near vision zones of constant power which contribute to the correction of the refractive error of the eye for a particular far or near distance.

Yet another object of the invention is to provide a constant edge thickness to the lens incorporating the invention or to provide constant semi-diameter to the surface incorporating the invention at a specified sagittal depth.

Yet another object of the invention is to produce a lens which will consistently provide the desired optical correction in the presbyopic or aphakic eye even if the lens decenters about the optical axis of the eye, especially with regard to the contact lens design of the invention.

These and other objects and advantages are accomplished by a multifocal lens configuration having a lens body with first and second surfaces, wherein at least one of the surfaces incorporates the invention and is defined three-dimensionally as being rotationally non-symmetric about the optical axis of the lens, and having what may be described in terms of polar coordinates as angular zones or sectors of differing curvature responsible for near, intermediate or distance vision or combinations thereof. The lens surface is by definition constructed of a plurality of individually defined semi-meridian sections radiating from the apical umbilical point on the lens surface at which the derivative of curvature vanishes. The plurality of defined semi-meridian sections form a continuous surface and each of the angular zones blend smoothly and without discontinuity into adjacent zones. Each of the curved semi-meridian sections may be differently and uniquely shaped, and is defined according to its shape and magnitude which may be constant within an angular zone or may vary within the angular zone in a continuous and regular manner.

The lens configuration will provide an accommodative effect simulating that of the non-presbyopic phakic eye over a full range of distances regardless of the size of the pupillary aperture. The lens configuration can be used in the design of an intraocular lens wherein one or both surfaces of the lens body may be provided with the novel surface of the invention such that the angular zones will contribute to the correction of the refractive error of the eye while also providing the desired accommodative effect. Similarly, the novel lens surface design may be incorporated into a contact lens, with the posterior surface of the contact lens conforming generally to the shape of the corneal surface of the eye. The particular angular extent of each of the angular zones of the lens surface design may vary to a great extent, thus giving a great amount of flexibility in the design of the multifocal lens for a particular patient.

BRIEF DESCRIPTION OF THE DRAWINGS

The above objects and advantages of will become more apparent from a reading of the description in conjunction with the drawings, wherein:

FIG. 1 is a schematic cross sectional view of an eye showing an intraocular lens in accordance with the invention which replaces the crystalline lens of the eye, and those light rays contributing to clear central vision from both far and near axial points, incident upon the cornea, refracted by the novel intraocular lens, and focused on the retina;

FIG. 2 is a representational plan view of a first preferred embodiment of the multifocal lens configuration in accordance with the invention showing the apical radii of curvature for the semi-meridian sections forming the novel surface thereof;

FIG. 9 is a representational plan view of yet another alternate embodiment of a multifocal lens configuration in accordance with the invention showing the apical radii of curvature for the semi-meridian sections forming the surface, wherein each of the angular zones on the lens surface is defined by a plurality of semi-meridian sections which vary progressively and continuously throughout each of the zones;

FIG. 10 shows a representational plan view of an alternate embodiment of a multifocal lens surface configuration usable in a contact lens showing the apical radii of curvature for the semi-meridian sections forming the surfaces, wherein the edge thickness of the lens body is maintained at a constant value as is the case when coaxial surfaces of revolution are employed, and-/or when incorporated as the posterior surface of the lens, provides a constant semi-diameter at the edge of the lens and an overall contour approximating that of the aspheric cornea, thereby facilitating a comfortable fit;

FIG. 11 is a perspective view of the lens as seen in FIG. 10, wherein the convex contact lens surface is represented as having all semi-meridian sections aspheric to enable maintenance of the constant edge thickness.

DETAILED DESCRIPTION OF THE INVENTION

Figure 3:
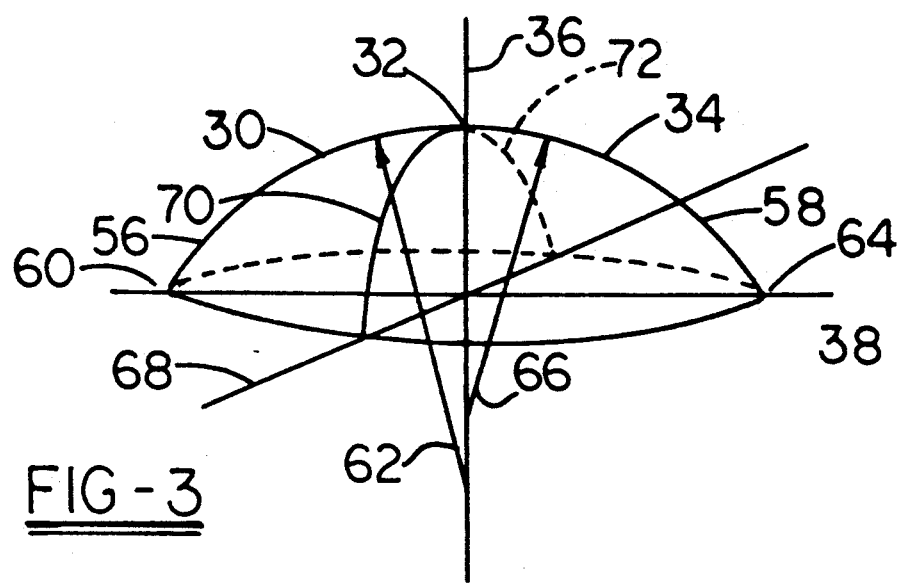
FIG. 3 is a perspective view of the lens as seen in FIG. 2 showing primary semi-meridian sections defining distance vision and near vision areas of the novel surface.

Turning now to FIG. 1, the novel intraocular lens 20 is shown, which takes the place of the absent crystalline lens in the eye 10. The intraocular lens 20 is positioned in the posterior chamber 22 of the eye normally found between the crystalline lens which has been removed from the eye, and the iris which is schematically shown at 24. Alternatively, the lens may be positioned in the anterior chamber of the eye. The pupil 26 defined by the iris 24 functions as an aperture to enable the proper amount of light to reach retina 12. A pupillary aperture 26 therefore changes depending upon the light conditions encountered, and will thus vary the amount of light passing through the intraocular lens 20 positioned in the posterior chamber 22. The diameter of the implanted intraocular lens 20 is normally significantly larger than the diameter of the pupil 26 so as to insure that all light passing through the pupil 26 will pass through the intraocular lens 20. In FIG. 1, the cross sectionally represented homocentric bundles of parallel light rays A from a distant axial point as well as diverging light rays B from a near axial point C are incident upon the cornea, and are refracted by the aqueous humor. The light rays then pass through the pupil 26 and are refracted by the novel lens 20 along the primary distance and near vision semi-meridian sections represented at right angles to one another along lines D—D' and E—E' respectively. Proceeding as converging bundles of light rays from the back surface of the lens, the rays are simultaneously brought to focus at the layer of the rods and cones of the retina 12 at F.

Alternatively, a contact lens may be provided which is positioned on the anterior surface of the cornea, such that light rays directed toward the eye will pass through the contact lens, and thereafter through the pupillary aperture 26 to be focused on the retina 12. It should be recognized that in most instances, the crystalline lens will not have been removed in the situation where the contact lens is used to correct the refractive error of the eye, and thus correction by the contact lens will take into account the degree of presbyopia of the patient. The contact lens will be positioned about the apex of the corneal surface such that light rays directed toward the eye will pass therethrough and may thereafter pass through the pupillary aperture 26 depending upon its size.

In both the use of the intraocular lens 20 or contact lens, it is desired to provide an accommodative effect simulating that of the non-presbyopic phakic eye. Such an accommodative effect will result in clear central vision over a continuous range of distances ranging from 6 meters and beyond to as close as 30 cm or perhaps nearer. It should be recognized that as the pupillary aperture 26 changes according to the amount of light entering the eye 10, the ability of the intraocular lens 20 or a contact lens to provide clear central vision over a full range of distance should remain substantially constant. Additionally, in both the use of an intraocular lens 20 or contact lens, it may be desired to minimize spherical and chromatic aberrations by utilizing convex surfaces characterized as flattening peripheralward in the optically active area along some or all semi-meridian sections or by utilizing concave surfaces characterized as steepening peripheralward in the optically active area along some or all of the semi-meridian sections so as to increase the resolving power of either lens.

Known spherical and aspherical surfaces of revolution conventionally used in intraocular or contact lens design have an apical umbilical point at which the derivative of curvature vanishes. These surfaces of revolution are defined as having a single central axial radius, or apical radius of curvature which, it follows, describe the infinitely many identical curved meridian sections defining the surface. The novel surface of this invention likewise has an apical umbilical point at which the derivative of curvature vanishes, but differs in that each curved meridian section may be differently and uniquely shaped, and is not necessarily symmetrical about the polar axis of the lens surface.

The term "apical radius of curvature" is used herein to define the apical curvature or magnitude of the individual semi-meridian sections comprising the three-dimensional figure of the lens surface. Each semi-meridian section or radial arc is further defined according to eccentricity, along with coefficients and exponents potentially modifying the conic shape of the semi-meridian sections. Each semi-meridian section may therefore be defined by the following polynomial:

$$Y=(2rx+(e^2-1)x^2)^{\frac{1}{2}}+Ax^F+Bx^G+Cx^H \qquad (1)$$

where y is defined as the distance in millimeters along a perpendicular from the polar axis to the semi-meridian section at any point along the surface. In the above equation, r is defined as the apical radius of curvature of the semi-meridian section, x is defined as the distance in millimeters from the apex or apical umbilical point of the surface along its polar axis, e is defined as the apical eccentricity of the semi-meridian section, A, B and C are constant co-efficients and F, G and H are constant exponents.

In the embodiments as will be hereafter described, the novel surfaces are defined three-dimensionally as being rotationally non-symmetric about the optical axis of the lens and may be described as having angular zones or sectors which define areas of the lens of differing curvature, each area responsible for near, intermediate or distance vision or combinations thereof. It should be recognized that this is merely for descriptive purposes and the lens surface itself will not have any visibly distinct zones thereon but will be a continuous smooth surface.

The surface design of the lens may be modeled graphically from two perspectives, firstly with respect to a plane perpendicular to the optical axis of the lens, similar to that of a circular plane section having a plurality of angular zones defined from the polar axis thereof. Secondly, the lens surface may be modeled in numerous planes containing the optical axis of the lens with the individually defined semi-meridian sections more specifically describing the surface contour, each as an individually mathematically defined arc radiating from the polar center and all simultaneously tangent at the polar center or apical umbilical point of the lens. Each of the semi-meridian sections or radial arcs may be constant or transitional in curvature, but the surface of the lens is itself aspheric due to its non-symmetry and variable angular power changes. The individual semi-meridian sections are preferably transitional in curvature or aspheric so as to reduce spherical and chromatic aberration and to increase visual resolution. The embodiments of the lens will provide the presbyopic or aphakic patient clear central vision over the described full range of distances as desired.

Figure 4:
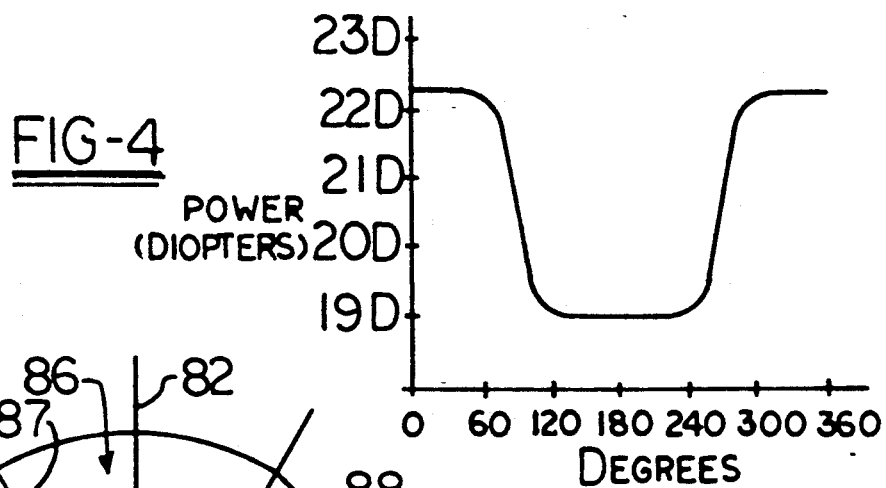
FIG. 4 is a plot of the refractive power of the lens surface with respect to the defined angular variation of the lens as seen in FIG. 2.

Turning now to FIGS. 2, 3 and 4 a first embodiment of the multi-focal lens configuration of the invention is shown. It should be understood that either one or both surfaces of the lens configuration may be provided with surface characteristics as defined by the invention to achieve the desired correction of refractive error and to provide the accommodative effect simulating that of the non-presbyopic phakic eye.

In FIG. 2, the surface 30 is seen represented graphically in two dimensions within a plane perpendicular to the optical axis 32 of the lens. Thus, in the plane of the paper, the lens surface 30 may be modeled as a circle having a plurality of angular zones or sectors defined from the optical axis 32 of the lens surface 30. The plurality of angular zones 40, 46, 52, and 54 define areas of the lens surface 30 having differing curvature and responsible for near, intermediate, or distance vision. Radiating centrifugally from the apical umbilical point 32 are a continuum of arcs of constant or transitional curvature defining semi-meridian sections of different magnitude and definition. The plurality of centrifugally radiating semi-meridian sections defining the continuous and smooth surface define the angular zones or sectors which are bi-symmetrical about bisector 38. The irregularly shaped closed FIG. 31 represented in FIG. 2, as well as in alternate embodiments of the invention described hereinafter, depict the length in millimeters of the apical radius of curvature for each of the semi-meridian sections defining the lens surface, and the variation in apical radius of curvature in terms of polar coordinates of the lens surface. The shape as shown in FIG. 2 and in subsequent figures does not represent the peripheral shape of the lens body which will be formed in accordance with the invention, but merely is a graphical representation facilitating the description of the invention, defining strictly the radii of curvature of the semi-meridian sections.

A first angular distance vision zone 40 is defined by lines 42 and 44 which depict planes containing the optical axis and apical umbilical point or polar center 32. The distance vision zone 40 will correct the refractive power of the aphakic eye to provide clear central vision for distances in the range from 6 meters and beyond. A second angular zone 46 defined by lines 48 and 50, forms a near vision zone, which will provide clear central vision for objects at distances as close as 30 cm. As seen in FIG. 2, both the distance vision zone 40, and near vision zone 46 have an angular extent of 120°, and therefore, approximately the same surface area.

Also in the lens surface design as seen in FIG. 2, two opposing intermediate distance vision zones 52 and 54 are defined between lines 42 and 48 for the zone 52 and lines 44 and 50 for zone 54. Each of intermediate distance vision zones 52 and 54 have an angular extent of about 60° and couple the distance vision zone 40 with the near vision zone 46 as seen in FIG. 2. The intermediate distance vision zones 52 and 54 and bi-symmetric about line 38 which is a bisector of distance vision zone 40 and near vision zone 46 respectively.

In the embodiment of FIG. 2, it may be desirable to maintain generally constant refractive power throughout both the distance vision zone 40 and near vision zone 46 of the lens, such that the semi-meridian sections defining each of the zones 40 and 46 may be of the same shape and magnitude throughout each of the individual areas. For a convex surface, to achieve the desired correcting refractive properties in each of the distance and near zones 40 and 46 respectively, the apical radii of the semi-meridian sections defining the distance vision zone 40 by necessity will be flatter than those of the near vision zone 46. In order to reduce the optical aberrations normally associated with spherical surfaces, it may be desirable to progressively flatten the surface peripheralward or to aspherize the arcs defining the semi-meridian sections comprising either or both the distance vision and near vision portions of the lens as well as those of the intermediate vision portions thereof.

As seen in FIG. 3, the surface 30 may be modeled in numerous planes containing the optical axis 36 of the lens, as individually mathematically defined semi-meridian sections 34 radiating from and simultaneously tangent to one another at the circular polar center or apical umbilical point 32. The depiction of the lens surface 30 as seen in FIG. 3 represents the two primary semi-meridian sections along a bisecting plane 38 containing the optical axis 36 of the lens surface 30 as seen in FIG. 2. The bisecting plane 38 thus shows a semi-meridian section 56 through the distance vision zone 40, originating at the axial polar center 32 of the geometric curve and extending to its end point 60 at the defined edge of the geometric curve. As an example, in a preferred embodiment of an intraocular lens, the apical radii of curvature of all of the semi-meridian sections defining the distance vision zone 40 of the lens surface 30 are identical and are 8.16 mm as defined by radius line 62 extending from polar axis 36.

The bisecting plane 38 also shows a semi-meridian section 58 extending and originating from the axial polar center 32 of the geometric curve and extending to its end point 64 at the defined edge of the geometric curve. The arc 58 defines the surface curvature of the near vision section 46. As an example, the near vision zone 46 is defined by identical semi-meridian sections throughout its extent, wherein the apical radii are 7.0 mm as shown by radius line 66. Also, as seen in FIG. 3, each of the semi-meridian sections 56 and 58 meet tangentially at the polar center 32 of the lens surface 30 to form the apical umbilical point at which the derivative of curvature of the surface 30 vanishes.

At a right angle to the bisecting plane 38 as seen in FIG. 2, is a bisecting plane 68 which intersects the intermediate vision zones 52 and 54 of the lens surface 30. The bi-symmetrical intermediate vision zones 52 and 54 are defined as being angularly transitional in power and curvature, ranging from equal to the distance zone at the points adjoining the distance zone along lines 42 and 44 as seen in FIG. 2. From this point, the intermediate vision zones 52 and 54 change in power and curvature to equal the curvature of the near vision zone 46 at the points adjoining the near vision zone along lines 48 and 50. The rate of change of power and curvature in the intermediate zones 52 and 54 may be progressive and regular and, generally speaking should be smooth, modeled by the section of a sine wave from $\pi/2$ to $3\pi/2$ as an example. The apical radii of curvature of all the semi-meridian sections defining the intermediate vision portions 52 and 54 of the lens, are not identical and progressively vary. For the examples given for the distance vision zone and near vision zone in the preferred embodiment, the apical radii of curvature within the intermediate vision zones will range from 8.16 mm to 7.0 mm. The semi-meridian sections 70 and 72 are equivalent and as modeled have an apical radii with a mean value of 7.58 mm in this example of the invention.

It should be recognized that although the embodiment as shown in FIGS. 2 and 3 specifies a bi-symmetrical surface configuration 30, the size of each of the angular zones making up the surface may differ from that shown. For example, the zones may comprise an angular extent less than 60° for each of the intermediate distance vision zones 52 and 54, and may instead provide an intermediate vision zone having an angular extent of 45° or some other variation. In this way, the angular extent of both the distance and near vision zones may be altered, thereby contributing more or less surface area to these distance ranges. Additionally, the angular extent of the distance vision zone 40 may be greater or lesser than that of the near vision zone 46, and the apical radii of the various semi-meridian sections in each of the various angular zones may differ from those stated.

Turning now to FIG. 4, there is shown a plot of the refractive power in diopters against the polar coordinates of the surface 30 as seen in FIG. 3. The plot 75 shows the transitional power change characteristic of an intraocular lens made of poly methyl methacrylate with an index of refraction of 1.491, and having a plane posterior surface and an anterior surface incorporating the novel surface 30 of FIG. 2. The zero degree indicia of the plot as seen in FIG. 4 starts at the location of the semi-meridian section 58 at point 64 as seen in FIG. 2, and extends clockwise traversing the surface 30 in an angular fashion. Thus, the plot 75 shows the refractive power of the lens first in a portion of the near vision zone 46 indicating a power of approximately 22¼ diopters. A 60° angular segment of the near vision portion 46 is traversed, after which the intermediate zone 52 shows a continuous and progressive decrease in power to the distance vision zone 40 occurring at the 120° mark. The distance vision zone 40 has an angular extent of 120° and is shown to be bisected by bisecting plane 38 extending through the polar center 32 of the surface and has a power of approximately 19 diopters. At the 240° polar coordinate, the second intermediate vision zone 54 begins, wherein the refractive power will increase continuously and regularly from distance vision zone 40 to near vision zone 46 beginning at the 300° mark. The remaining portion of the surface 30 has the constant refractive power of near vision zone 46. It is thus seen that each of the distance vision zone 40 and near vision zone 46 and combined intermediate vision zones 52 and 54 have angular extents of 120° with the intermediate zones 52 and 54 disposed between the distance and near vision zones. The intermediate vision zones have continuously and regularly varying refractive power from the adjacent distance vision zone to the adjacent near vision zone respectively.

Figure 5:
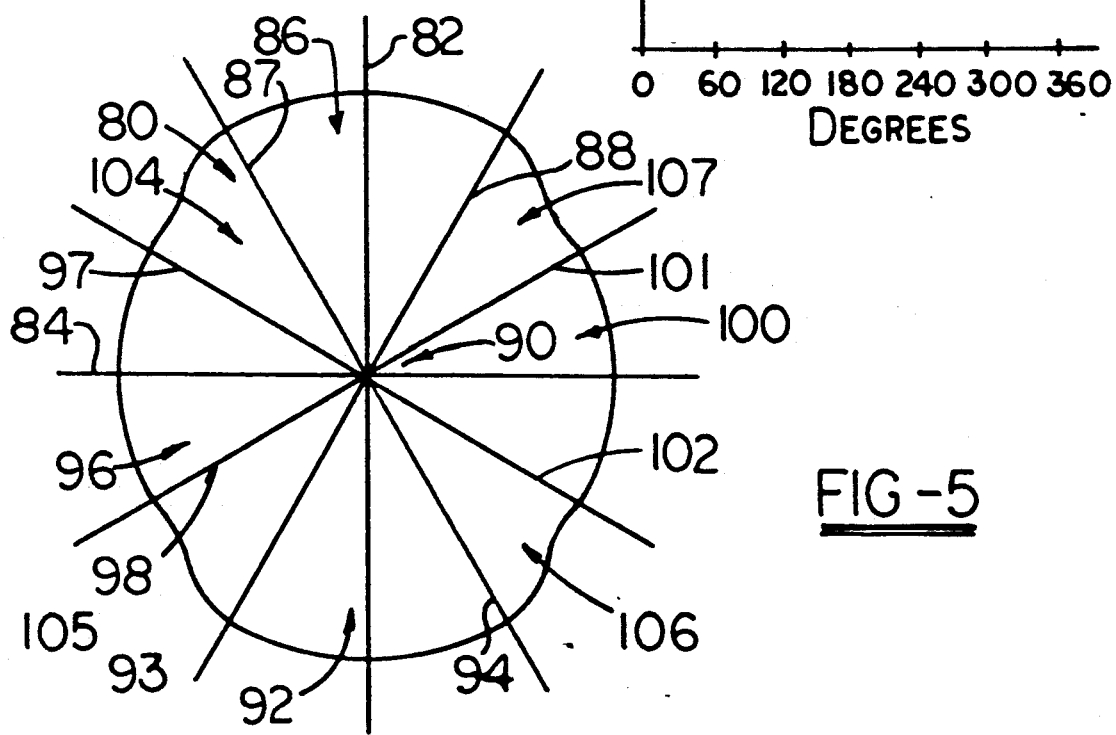
FIG. 5 shows a representational plan view of an alternate embodiment of a multifocal lens configuration in accordance with the invention, showing the apical radii of curvature for the semi-meridian sections forming the novel surface thereof.
Figure 6:
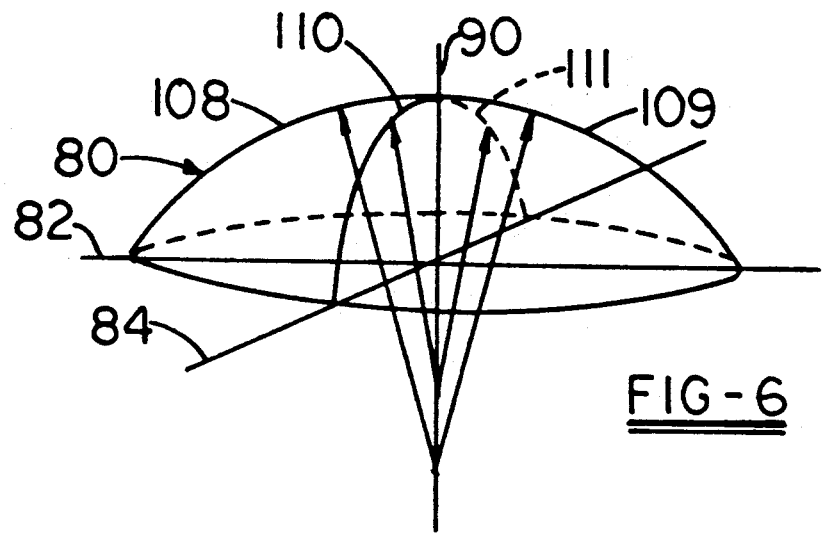
FIG. 6 shows a perspective view of the lens as seen in FIG. 5 showing primary semi-meridian sections defining distance vision and near vision areas of the lens surface, wherein the defined angular zones of the lens are symmetric about the polar axis of the lens.

Turning now to FIGS. 5 and 6, an alternate embodiment of the novel surface for the lens configuration of the invention is represented generally at 80 as being bi-symmetrical not only about a bisecting plane 82 but additionally about a bisecting plane 84 which is perpendicular to bisector 82. The symmetrical nature of the lens surface 80 creates mirror image quadrants or angular zones about each of the bisecting lines 82 and 84. In a preferred example, the surface 80 is designed as two pairs of radially opposing angular zones, each having specific optical characteristics, which separately and together provide correction for distant, intermediate as well as near object viewing. A first distance vision zone 86 is defined by lines 87 and 88, which when modeled in angular terms from the apical umbilical point or polar axis 90 of the lens surface form a distance vision zone 86 having an angular extent of about 60°. A second distance vision zone 92 is a mirror image of zone 86 about the bisector 84 and is defined by lines 93 and 94 forming a similar zone having an angular extent of about 60°. As in the embodiment of FIGS. 2-4, it may be desirable to maintain generally constant refractive power throughout the distance vision zones 86 and 92, wherein each semi-meridian section of each of the zones 86 and 92 will be defined by an arc having a constant apical radius of curvature, here demonstrated by the identical lengths along lines 87,88,93 and 94.

Additionally on surface 80 are provided a first near vision zone 96 bounded by lines 97 and 98 representing planes which contain the polar axis 90 of surface 80. A second near vision zone 100 is a mirror image of zone 96 about bisector 82 and is bounded by planes containing the polar axis 90 at lines 101 and 102. Each of the near vision zones 96 and 100 comprise an angular extent of about 60° similar to that of the distance vision zones 86 and 92 as previously described. The near vision zones 96 and 100 also may comprise generally constant power throughout each of these zones being comprised of identical semi-meridian sections having a constant apical radius of curvature throughout the zone, represented by identical lengths along lines 97,98,101 and 102.

The remaining portion of surface 80 comprises four separate intermediate distance vision zones 104, 105, 106 and 107 respectively, each of which lie between and adjacent to one of the distance vision zones and one of the near vision zones on the lens surface. Each of the intermediate vision zones 104-107 have an angular extent of about 30° and again comprise a plurality of semi-meridian sections which are radially transitional in power and curvature, ranging from equal to the adjacent distance vision zone to equal to the adjacent near vision zone at the points adjoining these zones. The rate of change of power and curvature in intermediate vision zones 104-107 may be progressive and regular, and again should be modeled to provide a smooth transition between the distance vision zone and near vision zone lying adjacent thereto.

As in the embodiment of FIGS. 2 and 3, the apical radii of curvature of the numerous semi-meridian sections defining the surface geometry are defined by the distance from the polar center 90 to specific points along the convoluted outline perimeter shape shown in FIG. 5 being a diagrammatic representation of the lens. As in the prior embodiment, the semi-meridian sections defining distance vision zones 86 and 92 may have an apical radii of curvature of 8.16 mm. The semi-meridian section defining near vision zones 96 and 100 may have an apical radii of curvature of 7.0 mm.

Turning now to FIG. 6, several of the primary semi-meridian sections in the defined angular zones of the lens surface 80 are shown. Specifically, the meridian sections along bisecting planes 82 and 84 are defined and extend through the symmetric distance vision zones 86 and 92 and the near vision zones 96 and 100 respectively. As should be evident from FIG. 6, the semi-meridian sections extending from polar center 90 to the edge of the lens surface in the distance vision zones 86 an 92, shown at 108 and 109, are identical and indicated as having equivalent apical radii of curvature. Similarly, the semi-meridian sections 110 and 111 formed along bisector 84, extend through the near distance vision zones 96 and 100 and have equivalent apical radii of curvature.

The semi-meridian sections 108 and 109 may also be defined based upon the polynomial of Equation (1) as having an apical radius of curvature, eccentricity, coefficients and exponent values as follows:

r=8.16
e=1.19,
A=−0.015,
B=0.02,
C=−0.0036,
F=1.64,
G=1.89,
H=2.52.

Similarly, symmetrically identical semi-meridian sections 110 and 111 define the two near vision sections 96 and 100 of the lens, and each may have an apical radius, eccentricity, coefficients and exponent values as follows:

r=7.0
e=1.22,
A=−0.008,
B=0.018,
C=−0.0032,
F=1.6,
G=1.85, and
H=2.4.

The following table lists the apical radii of curvature, eccentricity and constant coefficients and exponents at 5° increments from 30° to 60° for the semi-meridian sections comprising the intermediate vision section 105 as seen in FIG. 5. It should be recognized that each of the intermediate vision zones 104-107 may be substantially similar in nature to that described with reference to section 105 as extending between the adjacent distance vision zone and near vision zone.

TABLE I

| degrees | r | e | A | B | C | F | G | H |
|---|---|---|---|---|---|---|---|---|
| 30 | 8.16 | 1.19 | −.015 | .82 | −.0036 | 1.64 | 1.89 | 2.52 |
| 35 | 8.07 | 1.192 | −.0143 | .0199 | −.00357 | 1.637 | 1.887 | 2.512 |
| 40 | 7.84 | 1.197 | −.0126 | .0195 | −.0035 | 1.630 | 1.878 | 2.489 |
| 45 | 7.54 | 1.205 | −.0107 | .019 | −.0034 | 1.620 | 1.87 | 2.459 |
| 50 | 7.26 | 1.212 | −.0091 | .0185 | −.0033 | 1.610 | 1.86 | 2.429 |
| 55 | 7.07 | 1.218 | −.0083 | .0181 | −.00323 | 1.603 | 1.853 | 2.408 |
| 60 | 7.0 | 1.220 | −.008 | .018 | −.0032 | 1.6 | 1.85 | 2.400 |

The values for the intermediate vision zone 105 as recited in Table I describe a zone which is radially transitional in power and curvature wherein the change of power and curvature is progressive and regular from the distance vision zone to the near distance vision zone lying adjacent to zone 105.

Figure 7:
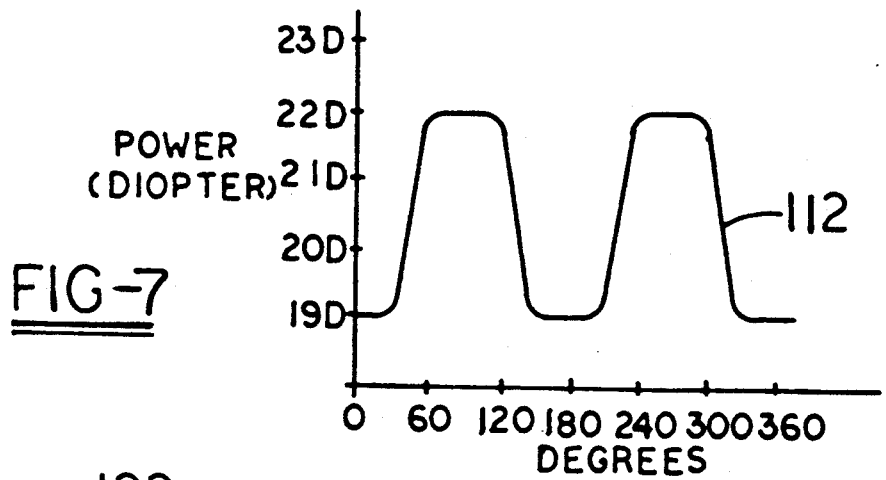
FIG. 7 shows a plot of the refractive power of the lens with respect to the defined angular variation for the lens as seen in FIG. 5.

Turning now to FIG. 7, there is shown a plot of the refractive power of the lens as shown in FIGS. 5 and 6 relative to the polar coordinates of the surface extending from bisector 82 in distance vision zone 92. The plot 112 shows the transitional power change characteristic of an intraocular lens made of poly methyl methacrylate with an index of refraction of 1.491, having a plane posterior surface and an anterior surface incorporating the novel surface design as shown in FIGS. 5 and 6. As the surface is rotationally traversed, the power in the distance vision zone 92 remains constant until the intermediate vision zone 105 begins at the 30° position relating to line 93 as seen in FIG. 5. The power within the intermediate vision zone 105 increases continuously and regularly over a 30° sector until the near distance vision zone 96 begins at the 60° position as indicated at line 98. The power within the near distance vision section 96 remains constant over a 60° sector until intermediate distance vision zone 104 begins at the 120° position. The power within intermediate distance vision zone 104 decreases progressively and regularly to the distance vision section 86 at 150° position as indicated at line 87. Over 30° of the distance vision section 86 shows the power within distance vision zone 86 to remain constant until the bisector 82 is reached within zone 86. The remaining portion of surface 80 is a mirror image of that just described.

In this embodiment as described, the desired clear central vision over the described full range of distances is achieved regardless of the size of the pupillary aperture as the contribution from each of the distance, intermediate and near distance zones of the lens surface will contribute proportionally equally to vision regardless of the size of the pupillary aperture. As the pupillary aperture is reduced, an equivalent portion of each of the defined angular zones is simultaneously reduced. Similarly, as the size of the pupillary aperture increases, an equivalent increasing portion of each of the defined angular zones will contribute to vision. It should further be evident that due to the bi-symmetrical nature of the defined angular zones of the design and the use of semi-meridian arcs of constant or transitional corrective curvature, the lens will continuously provide proper correction of the refractive error of the eye and the described accommodative effect even if the lens decenters from the optical axis of the eye. The nature of the present embodiment of the novel lens is such that any decentering of the lens and resulting removal of any portion of the lens body from the optically active area of the eye, will result in the introduction of a bi-symmetrically opposite lens body portion of equivalent power into the optically active area of the eye.

Figure 8:
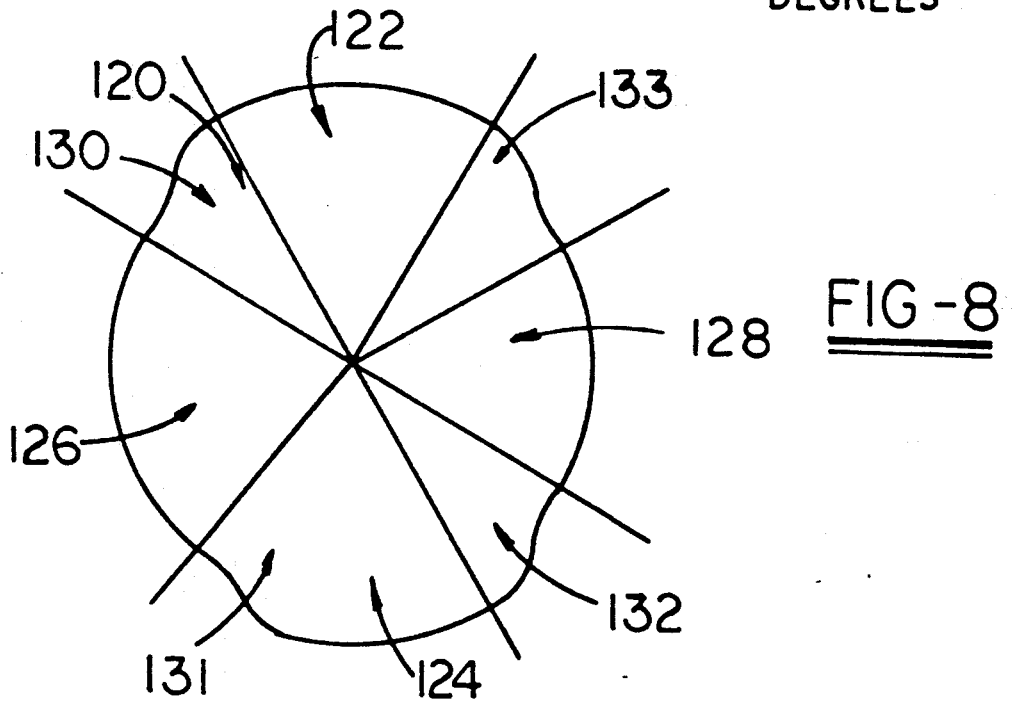
FIG. 8 shows a representational plan view of another alternate embodiment of a multifocal lens configuration in accordance with the invention showing the apical radii of curvature for the semi-meridian sections forming the surfaces, wherein the lens does not have the characteristic of bi-symmetry and the angular extent of the defined angular zones which contribute to distance and near vision are unequal.

Turning now to FIG. 8, there is shown an alternate embodiment of the novel lens which departs from the bi-symmetrical models previously described. In FIG. 8, the lens surface 120 again includes a plurality of defined angular zones having distinct or varying refractive properties contributing to the correction of the refractive error of the eye and providing an accommodative effect simulating that of the non-presbyopic phakic eye. The surface 120 comprises a first distance vision zone 122 and an opposing distance vision zone 124 which do not share a common bisector, and are also formed as being unequal in angular extent. Similarly, a first and second near vision zone 126 and 128 are provided in opposing positions on the lens surface, and also are unequal in angular extent and do not share a common bisector. Each of the opposing distance vision zones 122 and 124 are separated from the adjacent near vision zones 126 and 128 by intermediate vision zones 130-133.

The intermediate vision zones 130-133 again interconnect the distance vision zones with the near vision zones and are defined as being angularly transitional in power and curvature, ranging from equal to the distance vision zone at the points adjoining the distance zone to equal to the near vision zone at the points adjoining the near vision zone. It is noted that intermediate zones 130-133 all have an equal angular extent although it should be understood that the angular extent can vary if desired. It is also noted that intermediate vision zones 130 and 132 share a common bisector while intermediate vision zones 131 and 133 do not, but again there is no particular requirement for sharing a common bisector to achieve the advantages of the lens configuration herein.

Turning now to FIG. 9, there is shown a lens surface design with progressively and continuously changing apical radii of curvature within each of the angular zones defining the lens surface. Particularly, the lens surface 140 is modeled by an ellipse and forms a lens which will produce the desired correction of refractive error of the eye as in previous embodiments. As an example, the lens surface 140 with progressively and continuously changing radii may be modeled by an ellipse with a major axis of 16.32 mm and a minor axis of 14 mm. The lens surface 140 comprises first and second opposing distance vision zones 142 and 144, each having a 60° angular extent on surface 140. Similarly, first and second opposing near vision zones 146 and 148, each having an angular extent of 60°, are provided. Intermediate distance vision zones 150-153 lie adjacent to each of the distance vision zones and near vision zones and interconnect each of these zones as previously described. Each of the angular zones on lens surface 140 varies continuously and regularly throughout the individual zones and all of the semi-meridian sections making up each of the zones will therefore differ from one another.

Turning now to FIGS. 10 and 11, there is shown another embodiment of the invention which may be advantageously utilized in a contact lens configuration. In contact lens design, it is important to provide the aspects of wearability and comfort, while attempting to incorporate the variable power characteristics of the invention. In a contact lens, it may therefore be desirable to maintain a constant edge thickness or slope at the edge of the contact lens. Alternatively, or in conjunction with a constant edge thickness, it is desirable on the ocular surface to maintain a constant semi-diameter at a specified sagittal depth. To achieve these characteristics, aspheric arcs may be utilized to define at least some of the semi-meridian sections making up the lens surface. By utilizing aspherical arcs, a constant semi-diameter or Y-value may be realized at a specified final sagittal depth.

In FIGS. 10 and 11, there is shown a lens surface having constant semi-diameter values in the plane containing bisectors 165 and 166, as seen in FIG. 11, while also incorporating the plurality of angular zones have differing curvature and contributing to near, intermediate or distance vision. In the embodiment as shown in FIG. 10, the lens surface 160 includes first and second opposing distance vision zones 162 and 164 which are symmetrical about plane 165 and share a common bisector 166. Each of the distance vision zones 162 and 164 is shown to have an angular extent of 60°, which may vary if desired. The lens surface 160 also includes first and second opposing near vision zones 168 and 170 having 60° angular extents which are symmetrical about plane 166 and share common bisector 165. Each of the distance vision zones 162 and 164 and near vision zones 168 and 170 are bounded by adjacent intermediate distance vision zones 171-174. The distance vision zones and near vision zones may individually have generally constant refractive power. As an example, the distance vision zones 162 and 164 of a convex surface of a contact lens may comprise semi-meridian sections with apical radii of 7.7 mm while near vision zones 168 and 170 may be comprised of semi-meridian sections with apical radii of 7.4 mm. The intermediate distance vision zones 171-174 will preferably be angularly transitional in power and curvature, ranging from equal to the adjacent distance vision zone to equal the adjacent near vision zone as previously described.

The lens surface 160 as seen in FIG. 11 comprises a contact lens surface represented as having all semi-meridian sections defining surface 160 as being transitional in curvature or aspheric. Primary semi-meridian sections lying along the bisecting plane 166 of the distance vision zones 162 and 164 as well as bisecting plane 165 of the near vision zones 168 and 170 are shown. Along bisecting plane 166 through the distance vision zones 162 and 164 are formed two semi-meridian sections 176 and 177 which originate at the axial polar center 178 of lens surface 160 as previously described. In the embodiment as shown in FIG. 10, the semi-meridian sections 176 and 177 are equivalent within the respective distance vision zones 162 and 164. As an example, each of the semi-meridian sections 176 and 177 may be defined utilizing the polynomial values for Equation 1 as follows:

$r = 7.7$,
$e = 0.6092$,
$x = 1.495$,
$A = 0$,
$B = 0$,
$C = 0$,
$F = 0$,
$G = 0$,
$H = 0$

Based upon the foregoing polynomial values for the semi-meridian sections 176 and 177, the calculated value of Y is 4.65 mm relating to the distance indicated as A for semi-meridian section 176. Similarly, bisecting plane 165 of the near vision zones 168 and 170 forms two equivalent semi-meridian sections, one being referenced as 179. In order to maintain a constant edge thickness for a contact lens configuration, and based upon the example given above for the semi-meridian sections 176 and 177 in the distance vision zones 162 and 164, the polynomial values for the semi-meridian section 179 would be as follows:

$r = 7.4$,
$e = 0.627$,
$x = 1.495$,
$A = 0.005$,
$B = 0.008$,
$C = 0.017$,
$F = 1.6$,
$G = 2.4$,
$H = 3.2$

Based upon the polynomial values, the calculated value of Y for the semi-meridian section 179 is also 4.65 mm as indicated by the equivalent distance A for semi-meridian section 179. Based upon the above example for the semi-meridian sections in each of the distance and near vision zones of the lens surface 160, a contact lens configuration would be formed having a diameter of 9.3 mm with a constant edge thickness or semi-diameter as desired.

Figure 12:
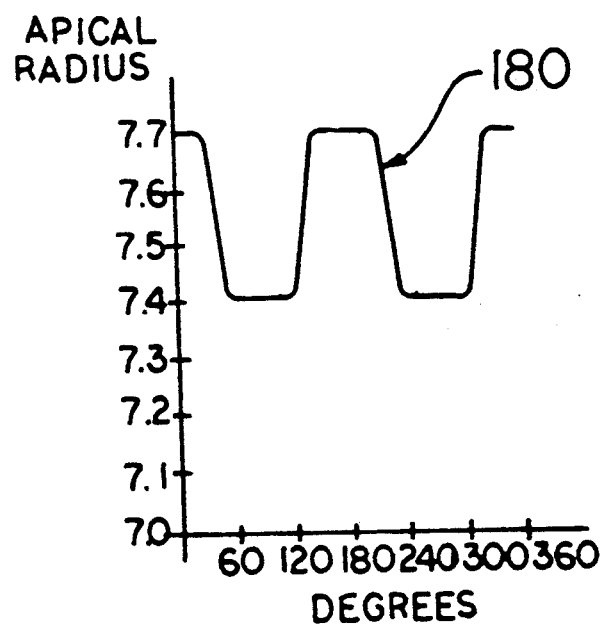
FIG. 12 is a plot of the apical radius of the curvature of the lens of FIG. 10 with respect to angular variation along the lens surface.

Turning now to FIG. 12, there is shown a plot 180 of the apical radius curvature of the semi-meridian sections in each of the angular zones making up lens surface 160 relative to the polar coordinates of surface 160 when rotationally traversing the surface clockwise from bisecting plane 166 within distance vision zone 164. As can be seen from plot 180, the values of the apical radii, r, begin at 7.7 mm until intermediate vision zone 172 begins where the apical radius varies regularly and continuously within zone 172 until near vision zone 168 is encountered with a r value of 7.4 mm. The apical radius of curvature remains constant within zone 168 until intermediate vision zone 171 begins. The r value increases continuously and regularly within zone 171 until distance vision zone 162 begins at which point the r value becomes 7.7 mm as in distance vision zone 164. The lens surface 160 is symmetrical about bisecting plane 166 and thus the variation in apical radius is similar in the remaining angular zones of surface 160.

In accordance with the embodiments of the invention as described, a computer program may be utilized to calculate the required polynomial values for a large number of semi-meridian sections of an intraocular lens or contact lens. Thus, a lens surface configuration in accordance with the invention may be computer modeled providing the ability to map or generate the surface on a computer numerical control profiling milling or grinding machine. It should be apparent that by designing the semi-meridian sections within both the distance vision and near vision zones individually as having identical and constant curvature and power, the generation of the lens surface might be simplified, but more importantly by defining each of the semi-meridian sections singly, a great amount of flexibility is possible in the lens design while achieving the desired optical characteristics.

Based upon the foregoing, a lens configuration of the invention may be utilized to form an intraocular lens of either the posterior or anterior chamber type, or a contact lens, which have one or more areas potentially optically corrected and contributing to distance vision, near vision or a range of intermediate vision accordingly. The surface generated in accordance with the invention may be applied either to the anterior or posterior surface or to both the anterior and posterior surfaces of an intraocular lens or contact lens. The radii defining the semi-meridian sections in the intraocular lens of this invention may range from infinity, describing a flat surface, to 4 mm such that the clear central vision of the patient is optimized. For example, either surface of an intraocular lens in accordance with the invention may comprise the novel surface including a plurality of the angular zones contributing to distance vision, near vision or a range of intermediate vision while the other surface of the lens is planar, convex spherical or aspherical, or concave spherical or aspherical. Similarly, both the anterior and posterior surfaces of an intraocular lens may comprise the generated surface in accordance with the invention which act together to contribute to the desired clear central vision over the described full range of distances. An intraocular lens in accordance with the invention may be made in a diameter and thickness consistent with conventional intraocular lens design, and when utilizing aspheric semi-meridian sections, may have instantaneous eccentricity values ranging from 0 to 4.0.

A contact lens configuration incorporating the invention may be generated using radii defining the semi-meridian sections of one or both surfaces of the lens which range from 4 mm to 30 mm, and selected such that the clear central vision of the patient is optimized. The anterior surface of the contact lens may be generated in accordance with the invention, and the posterior surface of the contact lens may be shaped to conform to the corneal surface of the eye and may comprise a surface in accordance with the invention. A contact lens may be generated to a center thickness and diameter consistent with conventional contact lens design while incorporating the novel surface of the invention as one or both surfaces thereof, and when utilizing aspheric semi-meridian sections, may have instantaneous eccentricity values ranging from 0 to 4.0. In both intraocular lens or contact lens design, the polynomial values for the coefficients A, B and C may range from −10.0 to 10.0 and values for exponents F, G and H may range from 0 to 10.0.

It will be evident to those skilled in the art that the invention is not limited to the details of the foregoing illustrative embodiments, and that the invention may be embodied in other specific forms without departing from the spirit thereof. It will thus be seen that the objects and advantages of the lens configuration in accordance with the invention may be achieved by modifying the embodiments described herein, and such modifications would be obvious to those of ordinary skill. It therefore is understood that the scope of the invention is only limited by the appended claims of the invention.

What is claimed is:

1. A multifocal lens configuration providing correction of the refractive error and accommodative insufficiency of the eye, comprising;

a lens body having first and second surfaces, wherein at least one of said surfaces is defined as being a rotationally non-symmetrical aspheric surface, said aspheric surface varying in curvature and refractive power rotationally about the apical umbilical point of the lens surface at which the derivative of curvature vanishes, with the surface contour defined by a continuum of mathematically defined semi-meridian sections tangent to one another at said apical umbilical point and which together form a continuous surface that includes at least four defined angular zones of predetermined curvature, wherein the semi-meridian sections in each of said at least four defined angular zones are varied in a predetermined manner to provide clear vision over ranges of near, intermediate, or distance vision.

2. A multifocal lens configuration as in claim 1, wherein, said at least one of said surfaces includes a plurality of angular zones providing at least one defined distance vision zone, at least two defined intermediate vision zones, and at least one defined near vision zone wherein the apical radius of said semi-meridian sections defining the surface curvature determine the required refractive properties for clear central vision at each of said corresponding distance ranges.

3. A multifocal lens configuration as in claim 2, wherein, said apical radii of said semi-meridian sections in said at least one distance vision zone are constant and said apical radii of said semi-meridian sections in said at least one near vision zone are constant.

4. A multifocal lens configuration as in claim 2, wherein, said apical radii of said semi-meridian sections in said at least one distance vision zone vary continuously and progressively and said apical radii of said semi-meridian sections in said at least one near vision zone vary continuously and progressively.

5. A multifocal configuration as in claim 2, wherein, at least two of said intermediate vision zones are provided between and adjacent to said at least one near and distance vision zones, and said apical radii of said semi-meridian sections in said at least two intermediate vision zones vary continuously and progressively ranging from the extreme values of the apical radii of both the near and distance vision zones.

6. A multifocal lens as in claim 1, wherein,
said lens is bi-symmetrical about one or more bisecting planes containing the optical axis of the lens.

7. A multifocal lens as in claim 1, wherein,
said at least one surface includes a plurality of angular zones which are symmetrical about the optical axis of said lens.

8. A multifocal lens configuration as in claim 2, wherein,
said at least one distance vision zone and said at least one near vision zone are equal in angular extent.

9. A multifocal lens configuration as in claim 2, wherein,
at least two intermediate vision zones are provided and are equal in angular extent to one another and have a total angular extent equal to one of said at least one distance vision zone and said at least one near vision zone.

10. A multifocal lens configuration as in claim 1, wherein,
said mathematically defined semi-meridian sections are each defined by the polynomial expressed as follows:

$$Y = (2rx + (e^2 - 1)x^2)^{\frac{1}{2}} + Ax^F + Bx^G + Cx^H$$

where Y is the distance in millimeters along a perpendicular line from said polar axis of said surface configuration to said surface, r is the apical radius of curvature of said semi-meridian section, x is the distance in millimeters from the apex of the surface at said apical umbilical point along its polar axis, e is eccentricity, A, B, and C are constant co-efficients, and F, G, and H are constant exponents.

11. A multifocal lens configuration as in claim 10, wherein,
the values of apical radius, eccentricity, A, B, C, F, G and H are chosen to minimize spherical and chromatic aberrations and to maximize clear central vision.

12. A multifocal lens configuration as in claim 5, wherein,
said mathematically defined semi-meridian sections defining said intermediate vision zones individually vary continuously and progressively with said polynomial values chosen to model said intermediate vision zones generally by the section $\pi/2$ to $3\pi/2$ of a sine wave.

13. A multifocal lens configuration as in claim 10, wherein in said polynomial
said apical radii of curvature of said semi-meridian sections range from 4 mm to infinity and have instantaneous eccentricity values ranging from 0 to 4.0, with said coefficients A, B and C ranging from −10.0 to 10.0 and said constant exponents ranging from 0 to 10.0 to describe a lens usable as an intraocular lens.

14. A multifocal lens configuration as in claim 10, wherein in said polynomial
said apical radii of curvature of said semi-meridian sections range from 4 to 30 mm and have instantaneous eccentricity values ranging from 0 to 4.0, with said coefficients A, B and C ranging from −10.0 to 10.0 and said constant exponents ranging from 0 to 10.0 to describe a lens usable as an contact lens.

15. A multifocal lens configuration providing clear central vision at various distances and correcting the refractive error of an eye, comprising;
a lens body having first and second surfaces, wherein at least one of said surfaces is modeled as having a plurality of angular zones including at least one distance vision zone, at least two intermediate vision zones, and at least one near vision zone, each of said zones defined by a plurality of predetermined semi-meridian sections which together form a continuous surface, wherein said semi-meridian sections defining each of said plurality of angular zones extend from the apical umbilical point of said at least one surface at which said semi-meridian sections are tangent and the derivative of curvature of the surface vanishes, such that each of said plurality of angular zones has predetermined refractive properties wherein said at least two intermediate vision zones lie between the adjacent to said at least one near and distance vision zones, with said semi-meridian sections defining said intermediate zones varying progressively in curvature from the adjacent semi-meridian section within said at least one adjacent distance vision zone to the adjacent semi-meridian section within said at least one adjacent near vision zone, such that said plurality of angular zones contribute to the correction of refractive error of an eye and together provide clear central vision over a range of distances from near to far.

16. A multifocal lens configuration as in claim 15, wherein,
said apical radius of curvature in said distance vision zone and said near vision zone is constant throughout these zones.

17. A multifocal lens configuration as in claim 15, wherein,
said apical radius of curvature in each of said distance vision zone and near vision zone vary continuously and progressively within each of said zones.

18. A multifocal lens configuration as in claim 15, wherein,
said semi-meridian sections defining each of said plurality of angular zones are defined by the polynomial expressed as follows:

$$Y = (2rx + (e^2 - 1)x^2)^{\frac{1}{2}} + Ax^F + Bx^G + Cx^H$$

where Y is the distance in millimeters along a perpendicular line from the polar axis of said surface configuration to the surface in each of said plurality of angular zones, r is the apical radius of curvature in each of said plurality of angular zones, x is the distance from the apex of the surface at said apical umbilical point to a point on the surface along its polar axis, e is the apical eccentricity, A, B, and C are constant co-efficients, and F, G and H are constant exponents wherein the values of apical radius, apical eccentricity, the co-efficients and exponents for the surfaces in each of said angular zones are chosen to minimize spherical and chromatic aberrations and maximize clear central vision in each of said zones.

19. A corneal contact lens for providing clear central vision at distance, intermediate and near distance ranges comprising;
- a lens body having concave posterior and convex anterior surfaces, each of said posterior and interior surfaces including an apical umbilical point at which the derivative of curvature of said surface vanishes,
- at least one of said surfaces being defined by a plurality of predetermined semi-meridian sections extending centrifugally from and tangent to one another at said apical umbilical point, said semi-meridian sections forming a continuous surface modeled as having at least four angular zones,
- said at least four angular zones including at least two angular zones having varying refractive properties defined by the predetermined changing curvature of said semi-meridian sections defining said at least two angular zones, such that clear central vision is achieved over a full range of distances regardless of the size of the pupillary aperture.

20. A corneal contact lens as in claim 19, wherein each of said semi-meridian sections defining said at least one lens surface is chosen to provide a constant edge thickness with respect to the other surface of said lens.

21. A corneal contact lens as in claim 19, wherein each of said semi-meridian sections defining said at least one lens surface is chosen to maintain a constant semi-diameter at a specified sagittal depth.

22. An intraocular lens for implantation in the eye providing clear central vision over distance, intermediate and near distance ranges comprising;
- a lens body having at least one surface comprising an apical umbilical point at which the derivative of curvature of said surface vanishes, wherein said surface is defined by a plurality of semi-meridian sections extending centrifugally from said apical umbilical point to form a continuous surface modeled as at least one defined angular zone, wherein said at least one angular zone will provide varying refractive properties defined by the curvatures of each of said semi-meridian sections, with said curvatures being varied in a predetermined manner such that the refractive power of said surface varies rotationally to provide clear central vision over a full range of distances regardless of the size of the pupillary aperture.

* * * * *